United States Patent
Okumura et al.

(10) Patent No.: US 6,193,372 B1
(45) Date of Patent: Feb. 27, 2001

(54) OPHTHALMOLOGIC APPARATUS

(75) Inventors: Toshiaki Okumura, Tokyo; Hiroshi Itoh, Utsunomiya, both of (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/472,821

(22) Filed: Dec. 28, 1999

(30) Foreign Application Priority Data

Dec. 30, 1998 (JP) .................................................. 10-377630
Dec. 10, 1999 (JP) .................................................. 11-352401

(51) Int. Cl.$^7$ ...................................................... A61B 3/10
(52) U.S. Cl. ............................................................ 351/221
(58) Field of Search ..................................... 351/205, 206, 351/208, 209, 210, 221, 211, 207

(56) References Cited

U.S. PATENT DOCUMENTS

| 5,270,749 | 12/1993 | Okumura | 351/211 |
| 5,500,696 | 3/1996 | Masuda et al. | 351/205 |
| 5,563,667 | * 10/1996 | Isogai | 351/221 |
| 5,751,396 | 5/1998 | Masuda et al. | 351/221 |
| 5,984,337 | 4/1999 | Okinishi et al. | 351/205 |

FOREIGN PATENT DOCUMENTS 7-31596   2/1995   (JP).

* cited by examiner

*Primary Examiner*—George Manuel
(74) *Attorney, Agent, or Firm*—Fitzpatrick, Cella, Harper & Scinto (57) ABSTRACT

An ophthalmologic apparatus which has namer for naming and designating an eye to be examined and the fundus portion of the eye to be examined, an examiner device for examining the fundus portion, a memory for storing therein a set state regarding the examination by the examining means of the named fundus portion, and a controller for controlling the examiner device to assume the set state on the basis of the stored set state when the fundus portion is designated by the namer, thereby being capable of effecting the next examination of the fundus of the eye within a short time.

18 Claims, 10 Drawing Sheets

REGISTER WINDOW FOR PORTION TO BE EXAMINED

NAME OF PORTION:

○ RIGHT EYE
○ LEFT EYE

○ ARTERY
○ VEIN

[REGISTER] [SUSPENSION]

FIG. 13

REGISTER WINDOW FOR PORTION TO BE EXAMINED

EXAMINEE ID:
abc201

LEFT EYE / RIGHT EYE

OPHTHALMOLOGIC APPARATUS

BACKGROUND OF THE INVENTION

1. Field of the Invention

This invention relates to an ophthalmologic apparatus for examining the fundus of an eye to be examined.

2. Related Background Art

As a retinal-blood-stream meter, a laser-Doppler blood-stream meter for tracking the blood vessel in the fundus of an eye to be examined, and measuring the blood-stream velocity in the tracked blood vessel has heretofore been disclosed, for example, in Japanese Patent Application Laid-open No. 7-031596. This laser Doppler, blood-stream meter is such that a laser beam for tracking is applied to an area including a blood vessel, and the reflected light thereof is amplified by an image intensifier, whereafter it is received as a blood vessel image by an image sensor, and the position of the blood-vessel is detected from this blood vessel image, and a galvanometric mirror is feedback-controlled so that the blood vessel may come to a predetermined position, thereby effecting tracking. At this time, the quantity of reflected light of the blood-vessel image differs greatly depending on the position or the like of the blood vessel in the fundus of the eye and therefore, the adjustment of gain becomes necessary.

Also, a laser beam for measuring the blood-stream velocity is applied to the tracked blood vessel in the fundus of the eye, and reflected light, Doppler-shifted by the Doppler effect, of blood corpuscles flowing in the blood vessel and the laser beam reflected from the tissue around the blood vessel or the like interfere with each other, and a beat signal corresponding to a Doppler shift frequency is received by a photomultiplier. At this time, the beat signal that is a reflection signal also differs greatly depending on the position of the blood vessel in the fundus of the eye and therefore, the adjustment of the gain is necessary. Besides this, there is also disclosed a blood-stream meter having the correcting function for adjusting the tracking position.

In the above-described retinal blood-stream meter according to the prior art, however, measurement values need be compared with one another with the lapse of time in the same region, and to measure the same region, the operation of photographing and marking the fundus of the eye during the first measurement, and performing the re-setting of the apparatus with the photograph of the fundus of the eye as reference during the next measurement is necessary. Therefore, there arises the problem that unless recording is done accurately, the measurement position will deviate delicately.

SUMMARY OF THE INVENTION

It is the object of the present invention to solve the above-noted problem and to provide an ophthalmologic apparatus which, when a portion measured or photographed in the past is to be measured again, can automatically set the last set value to thereby effect the measurement of the same portion easily within a short time.

To achieve the above object, the ophthalmologic apparatus according to the present invention is an ophthalmologic apparatus for effecting measurement or photographing to any portion of the fundus of an eye to be examined, characterized by detecting means for detecting the set state when the portion is to be measured or photographed, portion naming means for an examiner to add any non-overlapping portion name to the portion, examined eye data setting means for setting data specifying the eye to be examined, and memory means for storing therein the data set by the examined eye data setting means. The portion name given by the portion naming means and the set state detected by the detecting means are in association with one another.

Also, the ophthalmologic apparatus according to the present invention is an ophthalmologic apparatus characterized by naming means for naming an eye to be examined and a portion of the fundus of said eye to be examined, examining means for examining the portion of the fundus of the eye, memory means for storing therein the set state regarding the examination of the named portion of the fundus of the eye by the inspecting means, and control means for controlling the inspecting means to the set state on the basis of the stored set state when the portion of the fundus of the eye by the naming means is designated.

DESCRIPTION OF THE PREFERRED EMBODIMENTS

The present invention will hereinafter be described in detail with respect to some embodiments thereof shown in the drawings.

Figure 1:
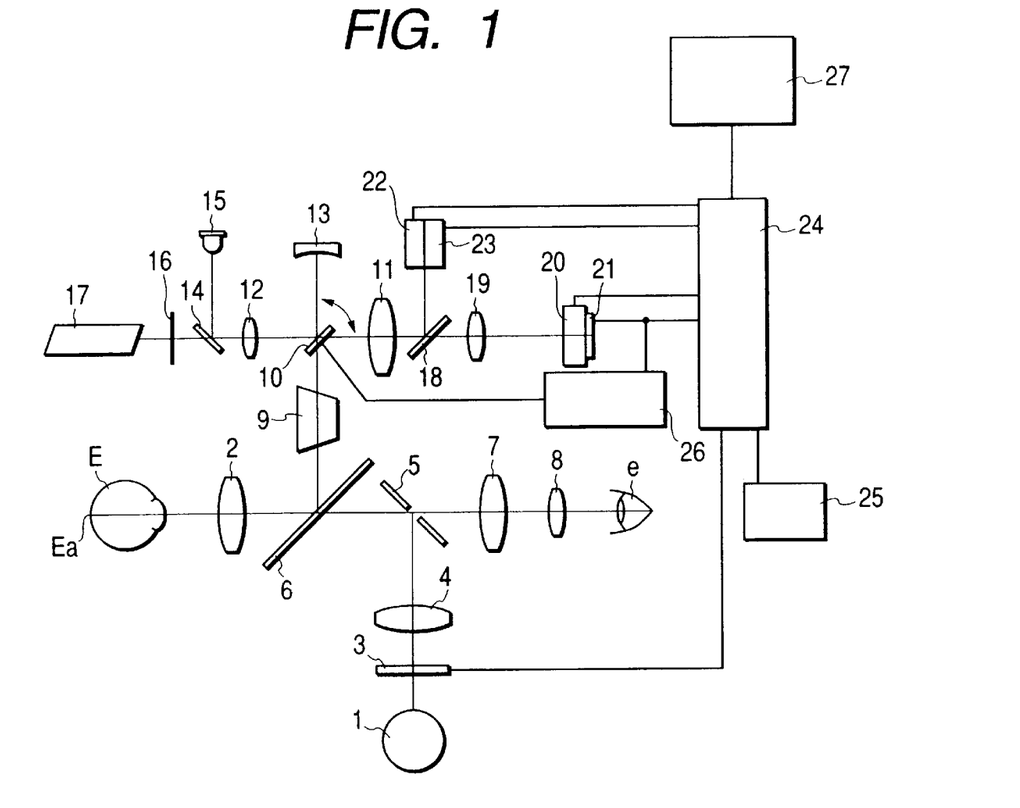
FIG. 1 shows the construction of a retinal blood stream meter according to an embodiment of the present invention.

FIG. 1 shows the construction of a retinal blood-stream meter according to an embodiment of the present invention. On an illuminating optical path leading from a light source 1 for observation comprising a tungsten lamp or the like emitting white light to an objective lens 2 opposed to an eye E to be examined, a transmitting-type liquid crystal plate 3, which is a fixation reference mark indicating element disposed at a position substantially optically conjugate with the fundus Ea of the eye E to be examined and movable along the optical path, a relay lens 4, an apertured mirror 5 and a band-pass mirror 6 transmitting light of a wavelength in the yellow range therethrough and almost reflecting the other light beams, are successively arranged. An eye-fundus observation optical system is constructed on an optical path behind the apertured mirror 5, and an imaging lens 7 movable along the optical path and an eyepiece 8 are arranged and lead to the eye e of an examiner.

An image rotator 9 and a galvanometric mirror 10, (light deflecting means) having a rotary shaft perpendicular to the plane of the drawing sheet of FIG. 1 and having both its surfaces polished, are arranged on the optical path of the band-pass mirror 6 in the reflecting direction thereof, a relay lens 11 movable along the optical path is disposed in the reflecting direction of the lower reflecting surface of the galvanometric mirror 10, and a lens 12 is disposed in the reflecting direction of the upper reflecting surface of the galvanometric mirror 10. The galvanometric mirror 10 has a cut-away portion below the rotary shaft thereof, and is disposed on the front side focal plane of a lens 12, which is in a conjugate relation with the pupil of the eye E to be examined.

A concave mirror 13 is disposed behind the galvanometric mirror 10 to thereby constitute a relay optical system for directing a light beam not reflected by the lower reflecting surface of the galvanometric mirror 10 but passing through the cut-away portion to the upper reflecting surface of the galvanometric mirror 10. A dichroic mirror 14 is disposed on the same optical path as that of the lens 12, and a light source 15 for measurement, such as a laser diode emitting, for example, collimated coherent red light, is disposed on the optical path of the dichroic mirror 14 in the reflecting direction thereof. Also, a mask plate 16 having a rectangular stop, and a light source 17 for tracking, such as a helium neon laser emitting, for example, red light differing from the other light source of high luminance, are arranged on the optical path of the dichroic mirror 14 in the transmitting direction thereof. A focus unit movable as a unit on the optical axis is formed by the dichroic mirror 14, the light source 15 for measurement, the mask plate 16, etc.

The relay lens 11, a dichroic mirror 18, a magnifying lens 19, an image intensifier 20 (light receiving sensor) and a one-dimensional CCD 21 (light receiving sensor) are successively arranged on the optical path of the galvanometric mirror 10 in the reflecting direction of the lower reflecting surface, whereby a blood-vessel detecting system is constituted. Also, photomultipliers 22 and 23 are disposed in the reflecting direction of the dichroic mirror 18, whereby a light-receiving optical system for measurement is constituted. For the convenience of illustration, all the optical paths are shown on the same plane, but the reflecting direction of the dichroic mirror 18, etc. are orthogonal to the plane of the drawing sheet of FIG. 1.

Further, a system controlling portion 24 for controlling the entire apparatus is provided, and an image intensifier 20, a one-dimensional CCD 21, photomultipliers 22, 23 and the output of input means 25 operated by the examiner are connected to this system controlling portion 24, the output of which is connected to a control circuit 26 for controlling the galvanometric mirror 10 and to an outside personal computer 27. Also, the transmitting-type liquid crystal plate 3, the imaging lens 7, and the relay lens 11 are adapted to be moved in the direction of the optical axis in operative association with one another by a focusing knob, not shown, being operated so that the fundus Ea of the eye E to be examined, the transmitting-type liquid crystal plate 3, the fundus of the examiner's eye e, the mask plate 16 and the light receiving surface of the image intensifier 20 may always become optically conjugate with one another.

By such a construction, the light beams emitted from the light sources 1, 14 and 16 are directed to the eye E to be examined, and the reflected scattered light thereof are directed to the examiner's eye e, the image intensifier 20, and the light receiving surfaces of the photomultipliers 22 and 23.

Figure 2:
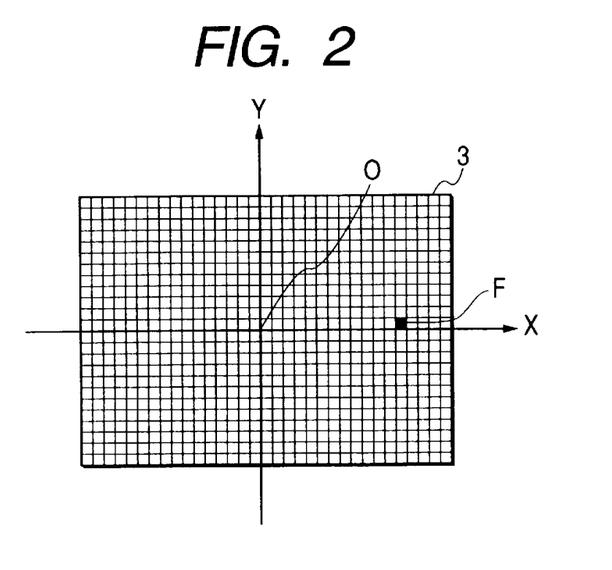
FIG. 2 is a front view of a transmitting type liquid crystal plate.

The white light emitted from the light source 1 for observation illuminates the transmitting-type liquid crystal plate from its back, passes through the relay lens 4 and is reflected by the apertured mirror 5, and only light of the yellow wavelength range is transmitted through the band-pass mirror 6, and passes through the objective lens 2 and is once imaged as an eye-fundus illuminating light beam image on the pupil of the eye E to be examined, and thereafter illuminates the fundus Ea of the eye substantially uniformly. At this time, a fixation reference mark F as shown in the front view of FIG. 2 is indicated on the transmitting-type liquid crystal plate 3, and this fixation reference mark F is projected onto the fundus Ea of the eye E to be examined by the illuminating light, and is presented as a fixation-reference-mark image F' to the examinee.

Figure 3:
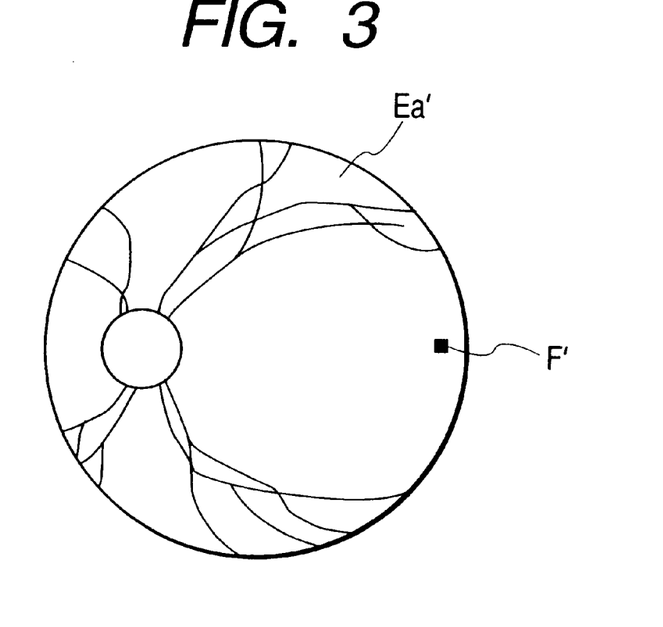
FIG. 3 is an illustration of the image of the fundus of an observed eye.

The reflected light from the fundus Ea of the eye returns along the same optical path, and is taken out as an eye fundus observation light beam from on the pupil, and passes through the central opening portion of the apertured mirror 5 and the imaging lens 7, and an eye fundus image Ea' as shown in FIG. 3 becomes observable by the examiner's eye e through the eyepiece 8. The examiner performs the alignment of the apparatus while observing the eye fundus image Ea'.

Also, the collimated measuring light emitted from the light source 15 for measurement is reflected by the dichroic mirror 14, while on the other hand, the tracking light emitted from the light source 17 for tracking is shaped into a desired shape by the mask plate 16, whereafter it is transmitted through the dichroic mirror 14. This measuring light and the tracking light pass through the lens 12, are reflected by the upper reflecting surface of the galvanometric mirror 10, and are further reflected by the concave mirror 14, and thereafter are returned toward the galvanometric mirror 10.

Here, the galvanometric mirror 10 is disposed at a position conjugate with the pupil of the eye E to be examined, and the concave mirror 14 is given the function of a relay system for imaging the galvanometric mirror 10 at −1 time and thus, the light beams reflected by the upper reflecting surface of the galvanometric mirror 10 are returned to the cut-away portion of the galvanometric mirror 10, and travel toward the image rotator 9 without being reflected by the galvanometric mirror 10.

The two light beams deflected toward the objective lens 2 by the band-pass mirror 6 via the image rotator 9 are applied to the fundus Ea of the eye E to be examined through the objective lens 2. As described above, the measuring light and the tracking light are reflected by the upper reflecting surface of the galvanometric mirror 10 and are again returned, and re-enter the galvanometric mirror 10 while being made eccentric from the optical axis of the objective lens 2 and therefore, irradiate the fundus Ea of the eye from a position eccentric relative to the center of the pupil.

The scattered reflected light of the measuring light and tracking light from the fundus Ea of the eye are again condensed by the objective lens 2, and almost all of the light beams are reflected by the band-pass mirror 6, pass through the image rotator 9, and are reflected by the lower surface of the galvanometric mirror 10, and pass through the relay lens 11, and the measuring light and the tracking light are separated from each other in the dichroic mirror 18.

The tracking light is transmitted through the dichroic mirror 18, and is amplified as a blood-vessel image Ev' magnified more than the eye-fundus image Ea' by the eye-fundus observation optical system by the magnifying lens 19, by the image intensifier 20, and thereafter is imaged on the one-dimensional CCD 21. On the basis of the blood vessel image Ev' picked up by the one-dimensional CCD 21, data representative of the amount of movement of the blood-vessel image Ev' is prepared in the system controlling portion 24, and the amount of movement of the blood-vessel image Ev' is outputted to the control circuit 26. The control circuit 26 drives the galvanometric mirror 10 so as to compensate for this amount of movement, thereby effecting the tracking of the blood vessel in the portion to be measured.

Also, the measuring light is reflected by the dichroic mirror 18, and is received by the photomultipliers 22 and 23. The outputs of the photomultipliers 22 and 23 are outputted to the system controlling portion 24, and the light-reception signal is frequency-analyzed and the blood-stream velocity in the fundus Ea of the eye is found.

Figure 4:
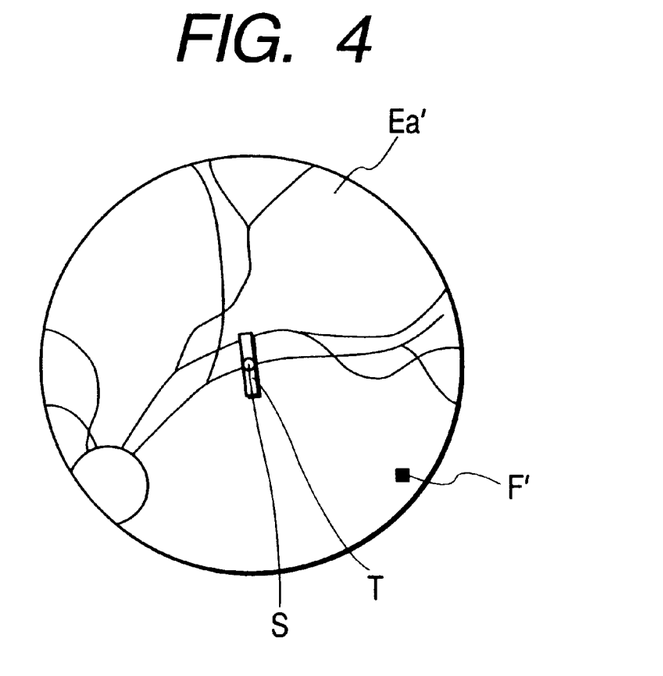
FIG. 4 is an illustration of the image of the fundus of the observed eye.

On the other hand, the scattered reflected light of the measuring light and tracking light from the fundus Ea of the eye are again condensed by the objective lens 2, and some of the light beam transmitted through the band-pass mirror 6 travels along an optical path similar to that of the reflected scattered light from the fundus Ea of the eye, of the light beam emitted from the light source 1 for observation and arrives at the examiner's eye e, and as shown in FIG. 4, with the observed eye fundus image Ea', a tracking reference mark image T and a measuring light image S become observable to the examiner.

Figure 5:
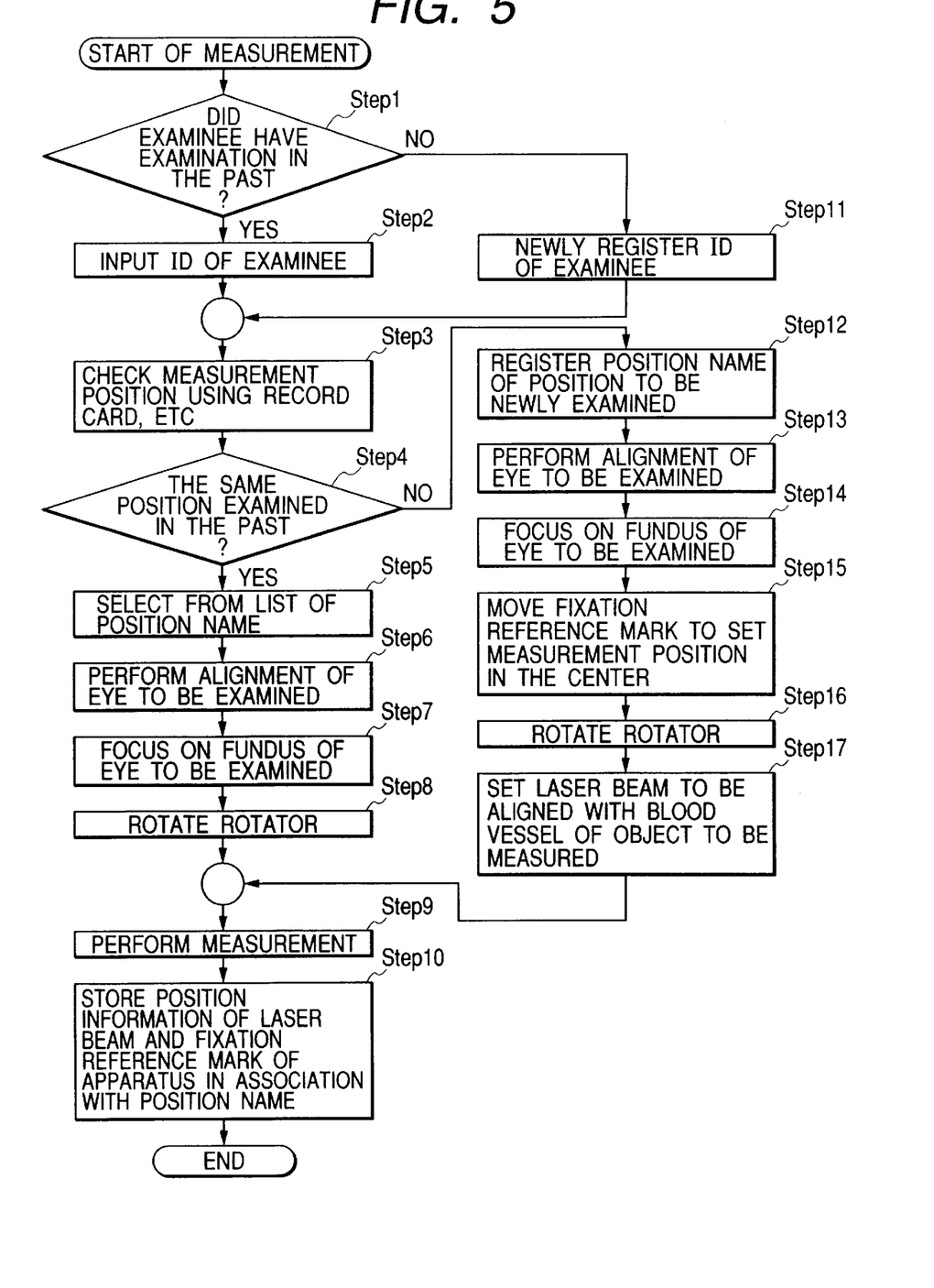
FIG. 5 is a flow chart of an operation procedure.

FIG. 5 shows a flow chart of the operating procedure. At the start of measurement, the power sources and software of the main body of the measuring apparatus and a personal computer are started. In the beginning, in the case of an examinee measured in the past, the examiner inputs his or her ID (step 1), and in the case of a new examinee, the examiner newly registers his or her ID (step 2), and adds (stores) the data to the examinee data base.

Figure 6:
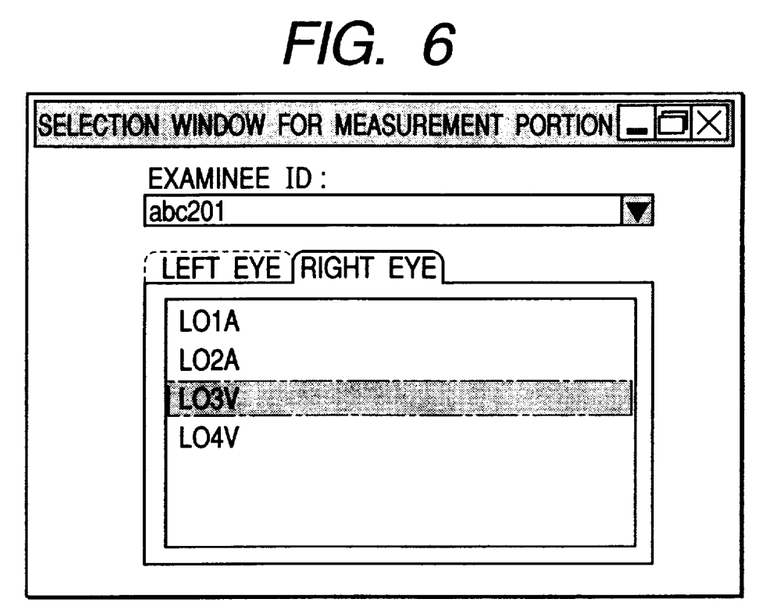
FIG. 6 is an illustration of a selection window for a measurement portion.

FIG. 6 shows a window on the screen of a personal computer 27 for selecting the examinee's ID, the right/left eye and the name of portion. First, the examiner inputs the ID of an examinee to be measured by this window through a keyboard, and then inputs the right/left of the eye E to be examined. If at this time, there is a portion measured in the past, the name of the measurement portion measured and registered in the past is displayed. In the present embodiment, the names of portions use numbers 01, 02, . . . , and L in L01A represents the left eye, 01 represents a number which does not overlap, A represents artery, R represents the right eye, and V represents vein. The examinee's ID corresponds to the inherent examinee's information, and L and R correspond to left and right eye information.

Figure 7:
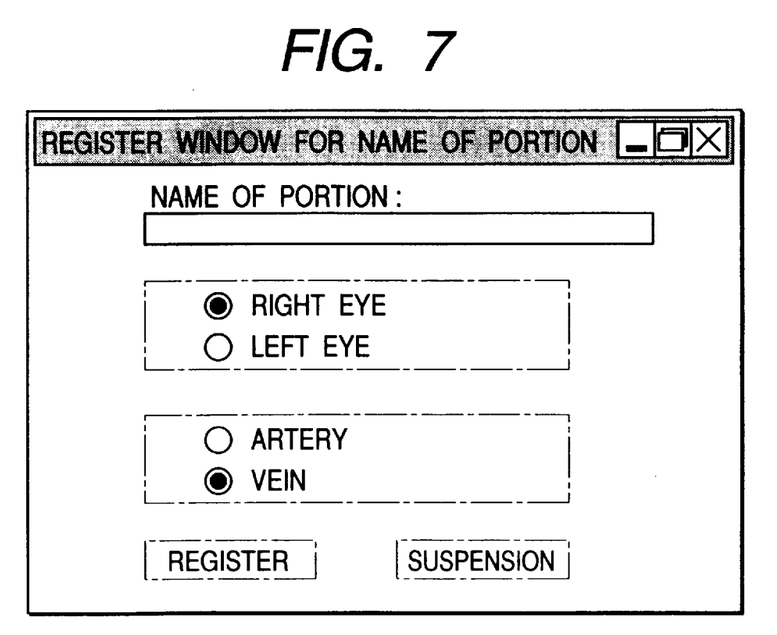
FIG. 7 is an illustration of a register window for the name of portion.

FIG. 7 shows a window for registering the name of measured portion to measure the first portion, and the name of any portion is selected and the distinction between the left and right and between artery and vein is inputted.

Next, the examiner confirms the portion to be measured this time with reference to the record card or the photograph of the fundus of the eye, and if the portion is a portion measured in the past, the portion to be measured is selected from the light of the names of portions in the window of FIG. 6, and the apparatus reads out the set condition of the name of that portion from the data base of measured portions (step 5).

When the name of a portion measured in the past is selected, the coordinates (position) of a fixation reference mark F, the angle of the galvanometric mirror 10 and the amplification factors of the image intensifier 20 and the photomultipliers (light receiving sensors) 22, 23, which are the set values of an apparatus measured in the past, are communicated from the personal computer 27 to the system controlling portion 24. The system controlling portion 24, which has received the set values, effects the setting of the apparatus on the basis of these set values.

Next, the examiner operates a control stick, not shown, to thereby effect alignment so that the optical axis of the eye E to be examined and the optical axis of the objective lens 2 may coincide with each other (step 6). Further, the examiner operates a focusing knob while observing the image Ea' of the fundus of the eye to thereby focus on the fundus Ea of the eye E to be examined (step 7). Thereby, the fixation reference mark F of the transmitting-type liquid crystal plate 3 and the fundus Ea of the eye become optically conjugate with each other and the fixation reference mark F is presented to the eye E to be examined, and the examinee fixates at the fixation-reference mark F', whereby it becomes possible for the examiner to observe the image Ea' of the fundus of the eye as shown in FIG. 3.

When at this time, the name of a portion measured in the past is selected, the fixation reference mark F is already set to the same position as the last one and therefore, the same position as the portion measured at the last time is immediately observed, and the measured portion becomes located substantially near the center of the field of view. Next, the examiner operates the input means 25 and applies tracking light to the fundus Ea of the eye, and operates a rotator operating knob, not shown, so that as shown in FIG. 4, a tracking-reference-mark image 32 may become perpendicular to the blood vessel to be measured, whereby the examiner can easily effect alignment with the same portion as the last one.

On the other hand, when the selected portion is a portion to be measured for the first time, the examiner needs to operate the input means 25 to thereby move the fixation-reference mark F so that portion to be measured may come to substantially the vicinity of the center of the field of observation, thereby inducing the eye E to be examined. Also, the examiner operates the input means 25 and applies the tracking light to the fundus Ea of the eye, and further operates the rotator operating knob so that a tracking-reference mark image T may become perpendicular to the blood vessel to be measured, and subsequently controls the angle of the galvanometric mirror 10 so that measuring light may be applied onto the blood vessel to be examined, whereby the image Ea' of the fundus of the eye as shown in FIG. 4 becomes observable (steps 13 to 17).

Next, the examiner effects the setting of the amplification factor of the image intensifier 20 to the blood vessel in the measured portion by the input means 25', and starts the tracking operation. The set value of the amplification factor of the image intensifier 20 greatly differs depending on the difference of the eye E to be examined and the difference of the measured portion. Accordingly, to accurately grasp the blood vessel and effect tracking, it is necessary to set the amplification factor to an optimum value, and this setting is automatically effected immediately before the start of tracking. However, when the same portion as the last one is to be measured, it is hardly necessary to re-set, and the tracking operation can be started immediately.

Subsequently, the setting of the amplification factors of the photomultipliers 22 and 23 is effected, whereafter the detection of a Doppler signal is effected for a predetermined time on end. The set values of the amplification factors of the photomultipliers 22 and 23, like the amplification factor of the image intensifier 20, greatly differ depending on the difference of the eye E to be examined and the difference of the measured portion. Accordingly, to accurately detect the Doppler signal, it is necessary to set the amplification factor to an optimum value, and this setting is also automatically effected immediately before the detection of the Doppler signal. However, when the same portion as the last one is to be measured, it is not necessary to re-set, and the detection of the Doppler signal can be started immediately.

The Doppler signal is outputted from the system controlling portion 24 and is inputted to the personal computer 27, whereby calculation and analysis are effected. After the Doppler signal has been detected for a predetermined time, the coordinates of the fixation reference mark F, the angle of the image rotator 9, the position of the focusing knob, the angle of the galvanometric mirror 10, and the amplification factors of the image intensifier 20 and the photomultipliers 22, 23, which are the set values of the apparatus, are transmitted from the system controlling portion to the personal computer 27.

These set values of the apparatus transmitted to the personal computer 27 are compared with the value of the last same portion stored in the personal computer 27, and if they deviate by a predetermined value or greater, it is warned to the examiner that the measured portion differs.

When the Examiner receives such warning, the examiner again confirms whether the measured portion has been wrong, and if it is not wrong, the examiner preserves the data and completes a cycle of measurement when there is no warning, the examiner preserves the data, assuming that the same portion as the last measured position has been measured, and completes a cycle of measurement.

Also, when the data is to be preserved, the set values of the measuring apparatus for the examinee's ID and the name of the measured portion are renewed and stored, and are used during the next measurement. In this manner, when the same portion as the last one is to be measured, the measurement of the same portion can be performed easily and within a short time, and the burden to the eye E to be examined can be reduced.

Figure 8:
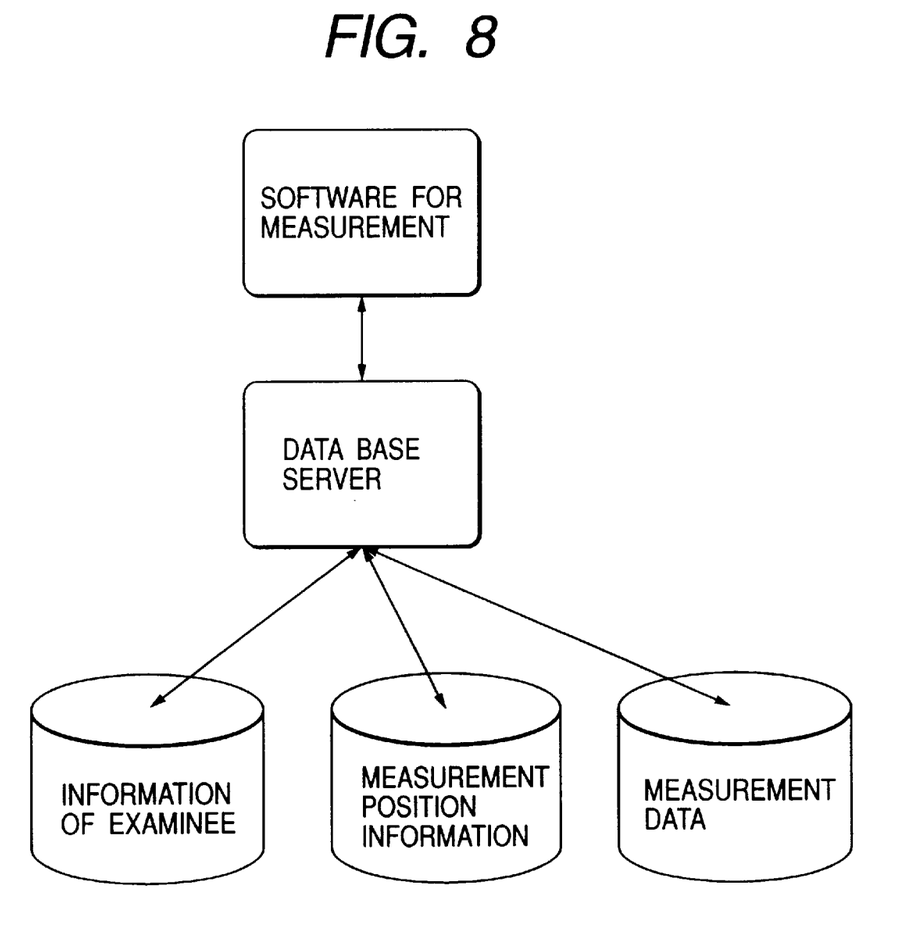
FIG. 8 shows the construction of data and a program.

FIG. 8 shows the construction of the data and program, and a relational data base is built with the examinee's ID as a key. An application program, which is the measurement software of the present embodiment, realizes the operation of the apparatus by accessing a data base server.

Table 1 below shows a data table regarding the information about examinees, and the examinees' ID, the names, sexes and dates of birth of the examinees, and the ID of doctors in charge are constructed as a record.

TABLE 1

| ID | Name | Sex | Dates of Birth | ID of Doctors in Charge |
|---|---|---|---|---|
| XYZ001 | nakamura | M | 1952/11/03 | dftg01 |
| ABCDEF | suzuki | F | 1930/03/21 | htvt02 |
| XYZ002 | tanaka | F | 1980/05/30 | adiv10 |
| ABCDEF | sato | M | 1959/09/18 | gifn38 |
| . | . | . | . | . |
| . | . | . | . | . |
| . | . | . | . | . |

Also, Table 2 below shows a data table regarding the measured portions, and the examinees' ID, the distinction of right/left (R/L) of the eye to be examined, the names of portions, the distinction of artery/vein (A/V), the horizontal coordinates X and vertical coordinates Y of the fixation-reference mark F, the information of focus (FC), the angles of rotation of the image rotation (IR) 9, the angles of rotation of the galvanometric mirror (GM) 10, the amplification factor of the image intensifier (II) 20, and the amplification factors of the photomultipliers (FM) 22, 23 are contracted as a record.

TABLE 2

| ID | R/L | Names of Portions | A/N | x coordinates of F | y coordinates of F |
|---|---|---|---|---|---|
| XYZ001 | R | 01 | A | −20.5 | −15.3 |
| XYZ001 | R | 02 | A | 10.5 | −10.0 |
| XYZ001 | R | 03 | V | 12.0 | 9.5 |
| XYZ001 | L | 13 | A | −15.0 | 5.5 |
| XYZ001 | L | 14 | V | 14.7 | 12.0 |
| ABCDEF | R | 01 | A | 18.0 | 14.0 |
| ABCDEF | R | 02 | V | −12.0 | −14.6 |
| ABCDEF | L | 01 | A | 16.0 | 5.5 |
| ABCDEF | L | 02 | V | 14.0 | 3.0 |

| ID | Position of FC | Position of IR | Position of GM | Amp. Factor of II | Comp. Factor of FM |
|---|---|---|---|---|---|
| XYZ001 | −0.25 | 30 | 5.1 | 56 | 88 |
| XYZ001 | −0.5 | 20 | 3.5 | 45 | 77 |
| XYZ001 | −0.75 | −15 | −5.2 | 78 | 68 |
| XYZ001 | −1.25 | −034 | 7.3 | 35 | 87 |
| XYZ001 | −1.5 | 12 | 2.4 | 76 | 89 |
| ABCDEF | −5.5 | 54 | −4.4 | 45 | 65 |
| ABCDEF | −6.0 | 76 | 2.2 | 35 | 57 |
| ABCDEF | −2.5 | −43 | 1.6 | 35 | 56 |
| ABCDEF | −2.75 | −54 | −6.6 | 33 | 34 |
| . | . | . | . | . | . |
| . | . | . | . | . | . |

For the ID of an examinee, the distinction between the right and left of the eye E to be examined and the name of portion, there is the set value of a set of apparatuses, and this set value is renewed at each cycle of measurement. In the present embodiment, numbers are given to the portion of the fundus Er of the eye, but names or the like comprehensible to the examiner may be given. Also, the focus information and the angles of rotation of the image rotator 9 have had their set values compared by manual operation, but for example, they can also be designed to be electrically moved and be automatically set like the fixation reference mark F.

A second embodiment of the present invention will now be described in detail.

Figure 9:
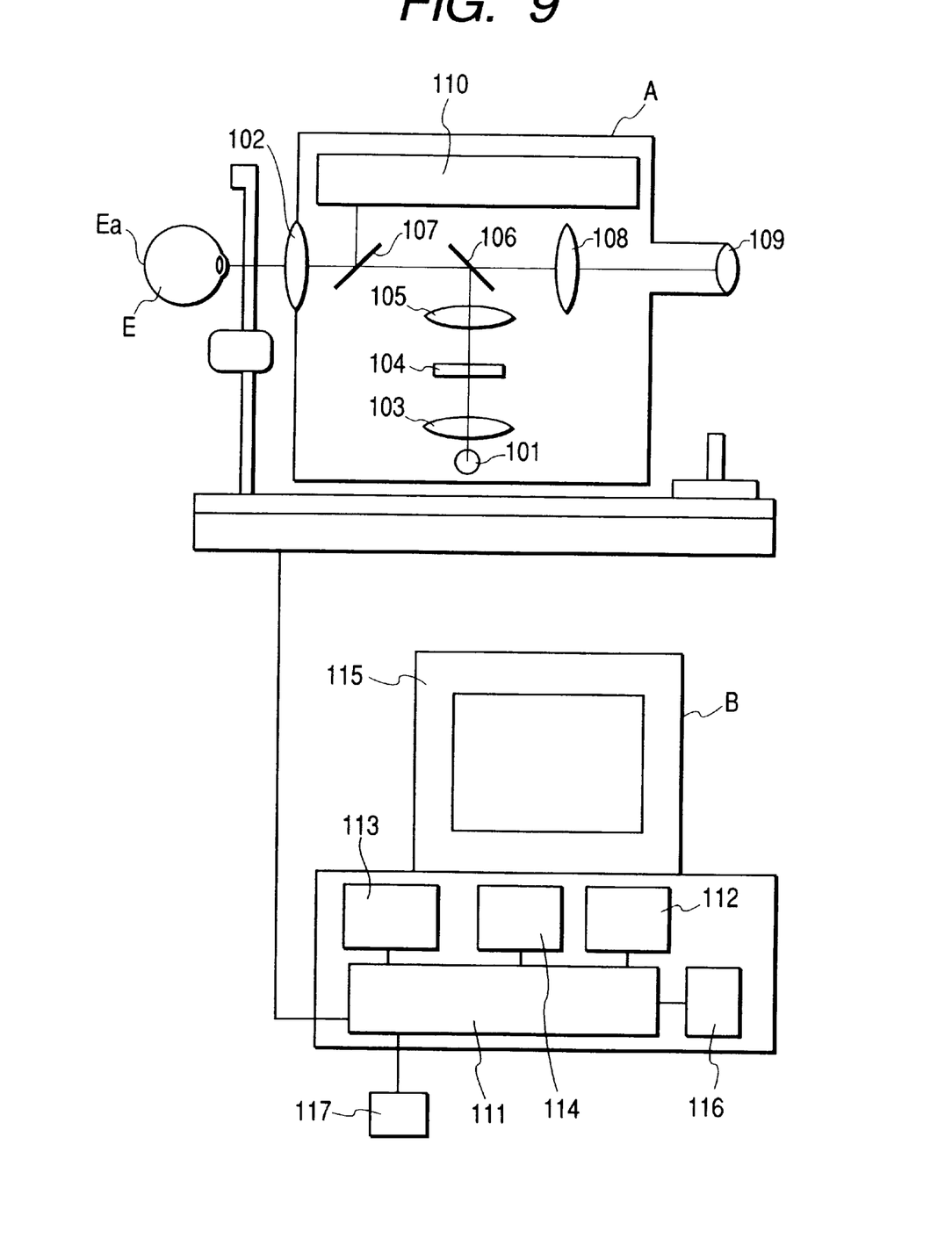
FIG. 9 shows the construction of an eye fundus examining apparatus according to an embodiment of the present invention.

FIG. 9 shows the construction of a retinal blood-stream meter according to the present embodiment, and the retinal blood-stream meter A is designed to present a fixation-reference mark to the eye E to be examined through a retina-illuminating optical system. In the retinal blood-stream meter A, in an illuminating optical system leading from a light source 101 for observation comprising a tungsten lamp or the like emitting white light to an objective lens 102 opposed to the eye E to be examined, a relay lens 103, a transmitting-type liquid crystal plate 104, which is a fixation reference-mark indicating element movable along the optical path, a relay lens 105, an apertured mirror 106 and a band-pass mirror 107 are arranged in succession. An eye-fundus observation optical system is constructed behind an apertured mirror 107, and an imaging lens 108 and a finder 109 having an eyepiece are arranged. Also, on the optical path of the band-pass mirror 102 in the reflecting direction thereof, there is disposed measuring and examining means 110 comprising an irradiating optical system for irradiating the fundus Ea of the eye with measuring light to measure the blood-stream velocity, and a light-receiving optical system for receiving the measuring light from the measured portion of the fundus Ea of the eye.

The retinal blood-stream meter A is connected to a personal computer B, which is provided with a control portion 111 for analyzing the output signal from the retinal blood-stream meter A and judging the presented position of the fixation-reference mark to the examined portion, and the output of the control portion 111 is connected to first memory means 112 storing therein whether a registered portion to be examined was examined in the past, second memory means 113 for storing therein the position of the fixation-reference mark during examination in association with the portion to be examined, detecting means 114 for detecting whether an already examined portion is in the same eye as the portion to be examined next, and a television monitor 115, and the outputs of determining means 116 for determining the portion to be examined next and input means 117, such as a switch and a keyboard, are connected to the control portion 111.

Figure 10:
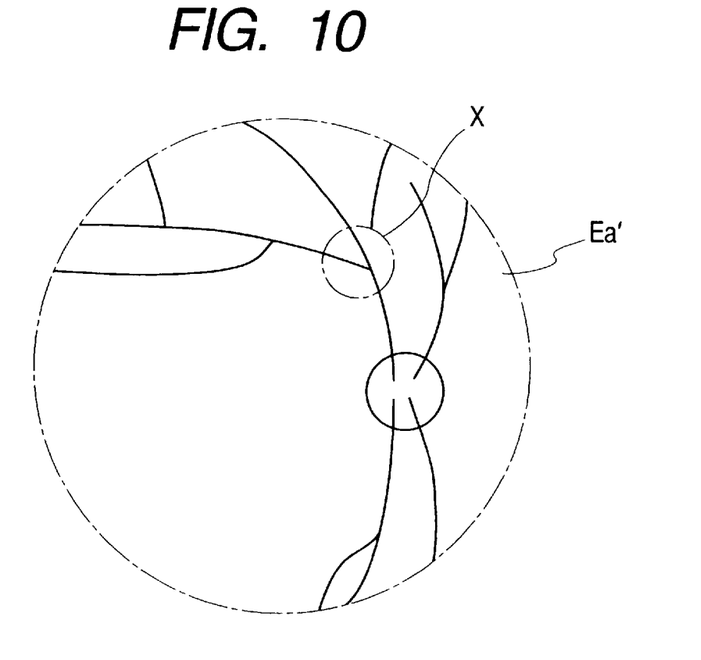
FIG. 10 is an illustration of the image of the fundus of an observed eye.

By such a construction, the light beam from the light source 101 for observation illuminates the fundus Ea of the eye E to be examined via the relay lens 103, the transmitting-type liquid crystal plate 104, the relay lens 105, the apertured mirror 106, the band-pass mirror 107 and the objective lens 102. The reflected light from the fundus Ea of the eye passes through the objective lens 2, the band-pass mirror 107, the aperture of the apertured mirror 106 and the imaging lens 108 to the eyepiece 109, and the examiner looks into the eyepiece of the finder 109 and performs alignment. Also, the light beam reflected by the band-pass mirror 107 comes to the measuring and examining means 110, and the eye fundus image Ea' as shown in FIG. 10 is received, and by this eye fundus image Ea' in the photograph of the fundus of the eye, the examiner performs the measurement, for example, of a portion X at which the blood vessel diverges.

Figure 11:
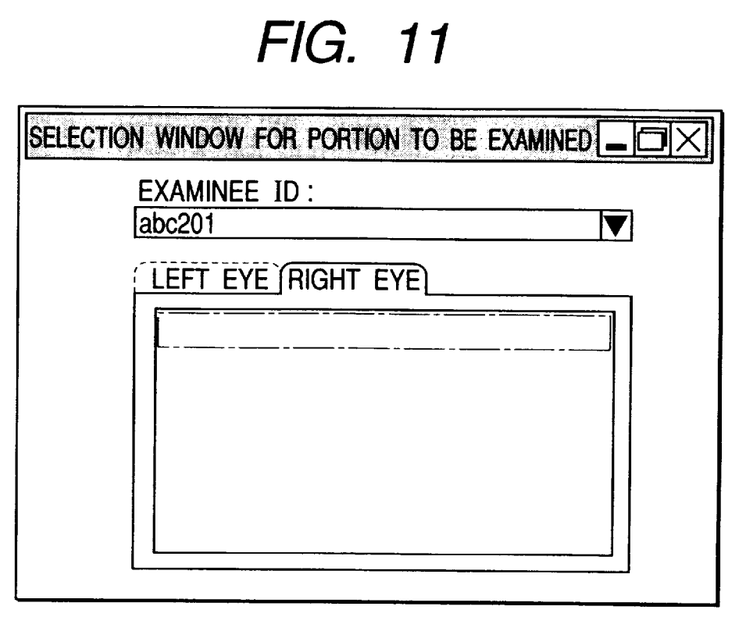
FIG. 11 is an illustration of a selection window for a portion to be examined.
Figure 12:
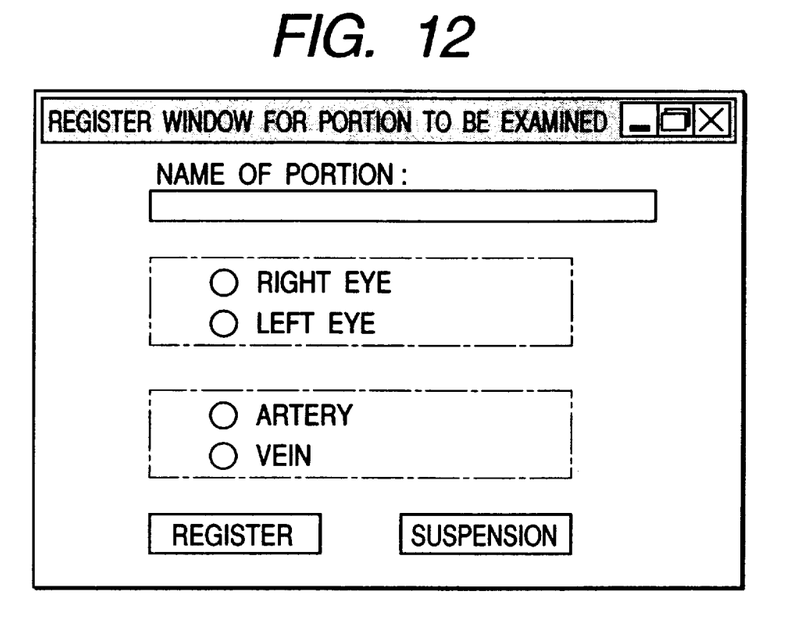
FIG. 12 is an illustration of a register window for the name of portion.
Figure 13:
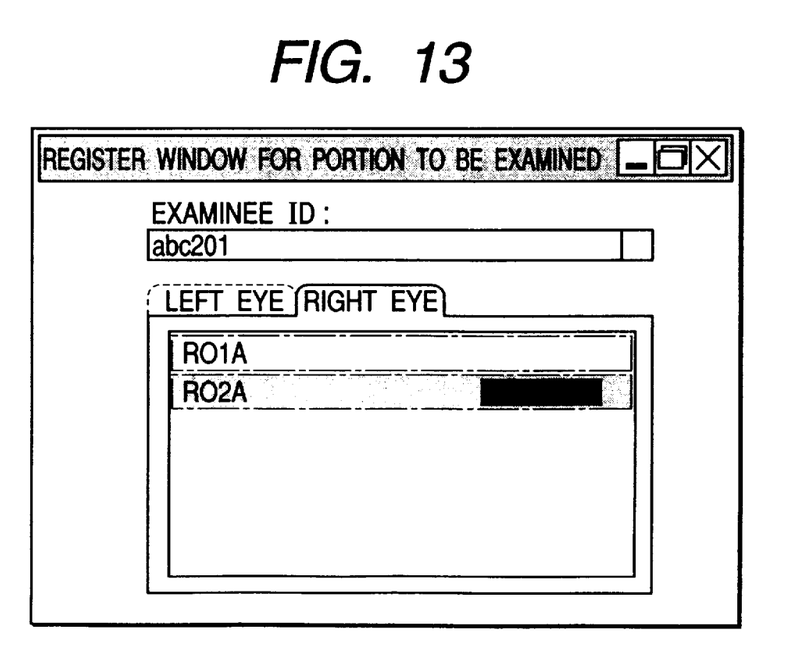
FIG. 13 is an illustration of a selection window for a portion to be examined.
Figure 14:
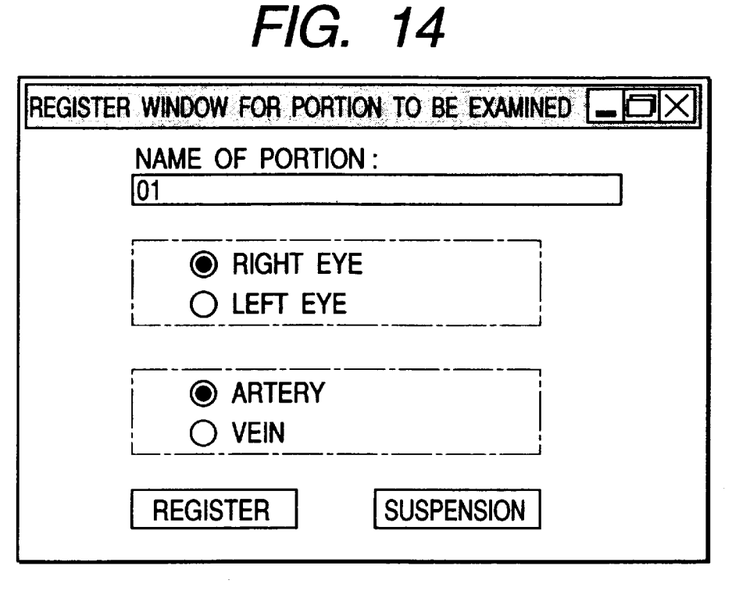
FIG. 14 is an illustration of a register window for a portion to be examined.

FIGS. 11 to 14 show window screens displayed on the television monitor 115 of the personal computer B, and more particularly, FIGS. 11 and 13 show selection window screens for a portion to be examined selecting the examinee's ID, right and left eyes and the name of portion, and FIGS. 12 and 14 likewise show register window screens for the name of portion. In FIG. 11, for example, "abc 201" is first inputted as the examinee's ID to be measured. Since this is the first measurement, there is no result of examination in the first memory means 112, and the lower right and left eye columns of FIG. 11 are blank.

In order to examine the first portion, the portion register window as shown in FIG. 12 is displayed as examined-portion register means for registering examined-portion data on the screen of the television monitor 115, and the examiner inputs the name of the portion, the distinction between the right and left of the eye E to be examined, and the distinction between an artery and a vein, i.e. "01, right eye R and artery A", as the examined-portion data, and selects a register button, whereupon as shown in FIG. 13, "R01A" is registered in the right-eye column of the selection window for the portion to be examined. Thereby, the determining means 116 determines "R01A" as the next portion to be examined, and this is displayed in the register window for the name of portion as shown in FIG. 14.

Figure 15:
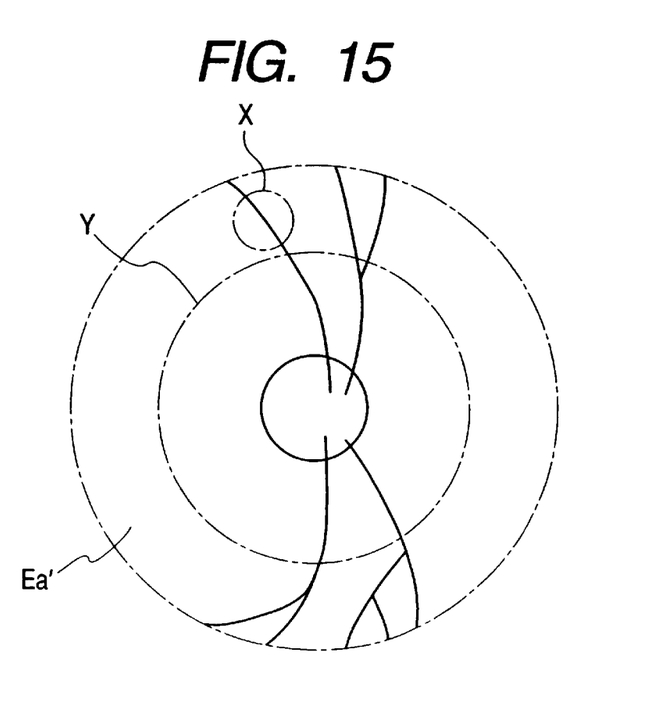
FIG. 15 is an illustration of the image field of the fundus of an observed eye.

Thereafter, the control portion 111 judges from the output of the detecting means 114 that there is no examined portion, and judges from the first memory means 112 that the next portion to be examined is an unexamined portion, whereupon the first fixation reference mark is presented at a position at which the optic disc of the eye E to be examined is substantially the center of the field of observation. FIG. 15 shows the eye-fundus image Ea' visually perceived through the finder 109 at this time. By the fixation-reference mark being thus controlled, the optic disc is at the center of the finder 109 and therefore, the running of the blood vessel is easy to pursue and a desired portion can be found out easily.

Figure 16:
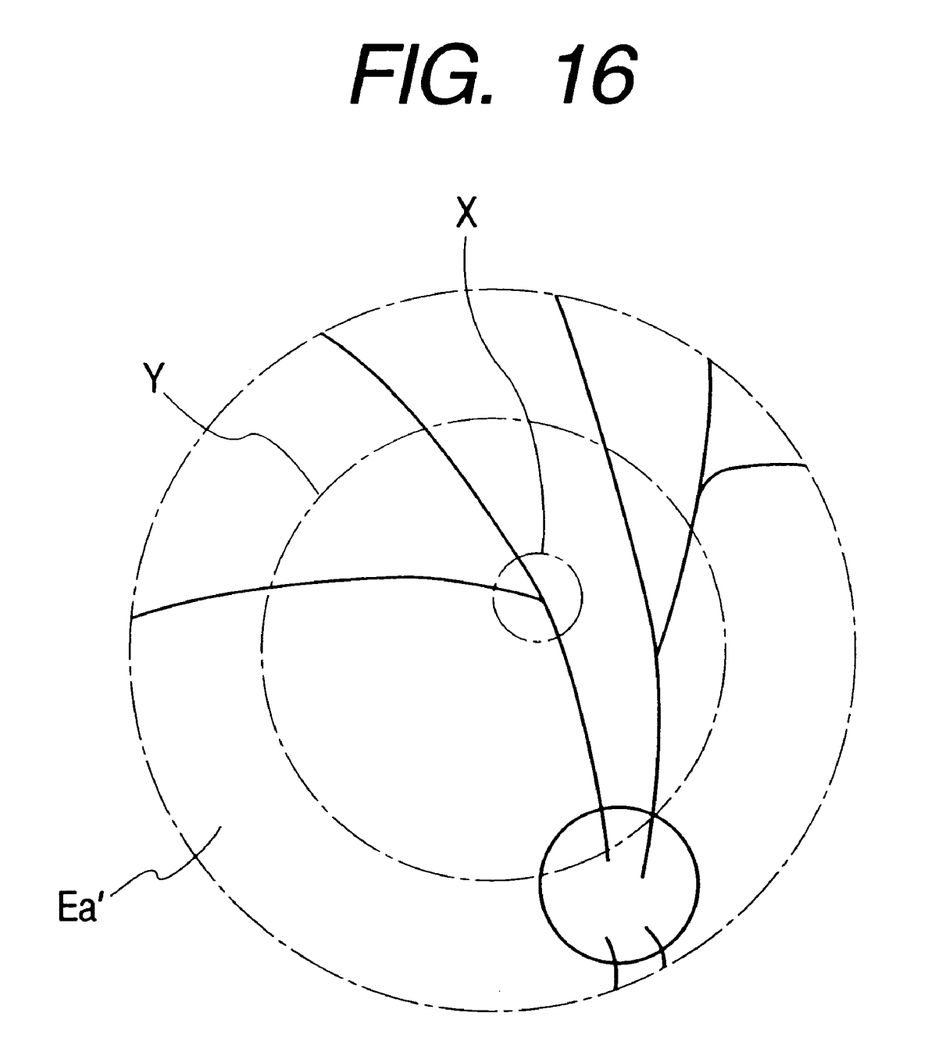
FIG. 16 is an illustration of the image field of the fundus of the observed eye.

Next, the examiner performs measurement with the position of the fixation-reference mark moved so that the desired portion X may fall within a measurable range Y, as shown in FIG. 16. At this time, the position of the fixation-reference mark during the measurement is stored in the second memory means 113 in association with the portion to be examined. At the same time, it is stored in the first memory means 112 that the measurement of the portion to be examined, i.e., "01, right eye R, artery A", has been effected, and it is detected by the detecting means 114 that there is an examined portion in the right eye R of "abc 201".

Subsequently, in order to measure the blood-stream velocity in the blood vessel after divergence as the next portion to be examined, the examined-portion register means for registering the measured-portion data is used to input "02, right eye R, artery A" and select the register button, whereupon as shown in FIG. 13, "R02A" is registered in the right-eye column of the selection window for the portion to be examined, and the determining means 16 determines the next portion to be examined as "R02A".

The control portion 111 judges from the first memory means 112 that the inputted "R02A" is an unexamined portion, and further judges from the output of the detecting means 114 that it is not the first portion to be examined but the second portion to be examined, and as the first presentation position, it reads but the fixation-reference-mark position during the measurement of the portion to be examined in the right eye immediately before, i.e., "R01A", from the second memory means 113, and effects the control of presenting the fixation reference mark.

In this manner, the examiner can finish the movement of the fixation-reference mark by fine adjustment and therefore can shorten the alignment time, and does not apply a load to the examinee. Again in the case of this measurement, the position of the fixation-reference mark "R02A" is stored in the second memory means 113 in association with the examined-portion data.

Next, the stage of the retinal blood-stream meter A is moved rightwardly to measure the left eye L. The operation thereafter is similar to that in the case of the right eye R, and "01, left eye L, vein V" is inputted to the register window for the name of a portion to be registered and the register button is selected, whereupon L01V is registered in the column of the left eye L in the selection window for a portion to be examined, and the determining means 116 determine the next portion to be examined as "L01V".

This measurement for this examinee is the third measurement, but the control means 111 receives from the detecting means 114 the result of the detection that there is a measured portion in the right eye R but there is no measured portion in the left eye L, and detects from the first memory means 112 that "01, left eye L, vein V" is not a measured portion, and outputs a signal for presenting the fixation reference mark at a position at which the optic disc of the left eye L comes to substantially the center of the field of observation. The presentation position of the fixation-reference mark during the next and subsequent examinations is similar to that in the case of the right eye R.

In order to measure the right eye R again, a similar procedure is taken for the examined portion register means to thereby register "R03A", whereupon the determining means 116 determines the next portion to be examined as "R03A". The control portion 111 receives from the first memory means 112 the output that "R03A" is not an examined portion, and receives from the detecting means 114 the output that there is an examined portion in the same eye, and as the first fixation reference mark presentation, it reads out the position of the fixation reference mark during the last time of "R02A" from the second memory means 113, and presents the fixation-reference mark.

Also, when the name of the portion measured in the past is selected in order to measure "R01A" again, the determining means 116 determines "R01A" as the next portion to be examined, and the first memory means 112 outputs that it is an examined portion, and the detecting means 114 outputs that there is an examined portion in the same eye. In response to the result of this output, the control portion 111 communicates the last position of the fixation-reference mark of "R01A" from the second memory means 113 storing therein the position of the fixation-reference mark in association with the portion to be examined, and presents the fixation-reference mark at that position of the fixation-reference mark.

Thus, in the present embodiment, if the next portion to be examined is an examined portion when the next portion to be examined is examined, the fixation-reference mark first presented is regarded as the position of the fixation-reference mark during the last examination, whereby it becomes unnecessary to move the fixation-reference mark. Also, when the next portion to be examined is an unexamined portion and there is no examined portion in the same eye, the optic disc is presented at the substantially central position of the field of observation, whereby the running of the blood vessel from the optic disc to a desired portion can be pursued and therefore, alignment becomes easy. Further, when the next portion to be examined is an unexamined portion and there is an examined portion in the same eye, the fixation-reference mark is presented at the position of the fixation-reference mark stored for the portion to be examined which has been examined immediately before, whereby it becomes easy to look for a desired portion when an artery and a vein diverging or proximate to each other are examined.

Also, when for example, the next portions to be measured are separate from each other like the nose side lower portion and the ear side upper portion of the optic disc, the examination time may become shorter if the optic disc is once brought to the center of the observation screen and is moved to a desired position while the running of the blood vessel is pursued. Accordingly, if fixation-reference mark position returning means is provided and the design of the device is made such that by inputting this fixation-reference-mark returning means, the position of the fixation-reference mark first presented becomes a position at which the optic disc comes to substantially the center of the field of observation, the examination time can be shortened and the burden to the examinee can be mitigated.

In the present embodiment, numbers 01, 02, . . . are used as the names of portions, but names comprehensible to the examiner may be given. Also, when for example, a plurality of diverging points on the fundus Ea of the eye are to be measured, it is more convenient to once return a diverging point to the center of the optic disc when shift is made from the diverging point to the next one and therefore, in the case of the second and subsequent unexamined portions, the fixation reference mark during the measurement of the same eye immediately before is used, but it will be more effective if the control of utilizing a switch 117, as the fixation-reference-mark returning means, and presenting the fixation-reference mark at a position at which the optic disc of the eye to be examined comes to substantially the center of the field of observation when the examiner inputs the switch 117, is effected.

As described above, the ophthalmologic apparatus, according to the present invention, when re-measuring a portion measured in the past, can automatically set the last set value to thereby effect the measurement of the same portion easily within a short time, and can prevent the mistake of a portion to be measured and improve the reliability of data, and further can reduce the burden to the eye to be examined.

Or even when prior to the start of an examination, the data of unexamined portions are registered by the names of portions to be examined and a portion to be examined is selected from the registered portions to be examined and the next portion to be examined is determined to thereby examine the divergence or the same portion of the blood vessel on the fundus of the eye to be examined a plurality of times, the result of the examination can be kept in custody for each portion to be examined and therefore, it never happens that to which portion the result of the examination corresponds becomes unclear.

What is claimed is:

1. An ophthalmologic apparatus for effecting examination for any portion of the fundus of an eye to be examined, comprising:

detecting means for detecting the set state of said ophthalmologic apparatus when said portion is examined, portion naming means for providing a non-overlapping desired portion name to said portion, examined eye data setting means for setting data for specifying the eye to be examined; and memory means for storing therein the data set by said examined eye data setting means, wherein the giving of the portion name by said portion naming means and the detecting of the set state by said detecting means are performed in association with one another.

2. An ophthalmologic apparatus according to claim 1, further comprising comparing means for designating the examined eye data and the portion name stored in said memory means when the same portion as the last one is to be examined, thereby comparing the set state stored correspondingly to said examined eye data and said portion name and the set state during the current examination with each other, and informing means for informing the examiner of the result of said comparing by said comparing means.

3. An ophthalmologic apparatus according to claim 1, further comprising re-setting means for designating the data of the eye to be examined and the portion name stored in said memory means when the same portion as the last one is to be examined, thereby re-setting the set state stored correspondingly to said data of the eye to be examined and said portion name.

4. An ophthalmologic apparatus according to claim 1, further comprising a fixation target for inducing the fixation of the eye to be examined, and wherein the presentation position of said fixation target is detected by said detecting means.

5. An ophthalmologic apparatus according to claim 1, futher comprising light beam deflecting means for deflecting a light beam for effecting the examination, and wherein the state of said light beam deflecting means is detected by said detecting means.

6. An ophthalmologic apparatus according to claim 1, further comprising focusing means for effecting focus adjustment to the fundus of the eye to be examined, and wherein the state of said focusing means is detected by said detecting means.

7. An ophthalmologic apparatus according to claim 1, further comprising light beam projecting means for projecting a light beam onto the fundus of the eye to be examined, and light receiving means capable of receiving scattered light from the fundus of the eye by said projected light beam and arbitrarily setting amplification factor information for photoelectrically converting the scattered light, and wherein the information set by said light receiving means is detected by said detecting means.

8. An ophthalmologic apparatus according to claim 1, wherein the data set by said examined eye data setting means are identification data for specifying an examinee and the distinction between the right and left of the eye to be examined.

9. An ophthalmologic apparatus according to claim 8, further comprising a fixation target to be presented to the eye to be examined, and wherein said memory means stores the fixation position of said fixation therein.

10. An ophthalmologic apparatus comprising:
   naming means for naming and designating an eye to be examined and the fundus portion of said eye to be examined,
   examining means for examining the fundus portion,
   memory means for storing therein the set state regarding the examination by said examining means of the named fundus portion; and
   control means for controlling said examining means to assume said set state on the basis of said stored set state when the fundus portion is designated by said naming means.

11. An ophthalmologic apparatus according to claim 10, wherein said examining means has a light receiving sensor for receiving the light from the fundus portion, and light deflecting means for directing the light from a desired fundus portion to said light receiving sensor, and wherein said memory means stores an amplification factor of said light receiving sensor therein.

12. An ophthalmologic apparatus according to claim 10, wherein said examining means has a light receiving sensor for receiving the light from the fundus portion, and light deflecting means for directing the light from a desired fundus portion to said light receiving sensor, and wherein said memory means stores the light deflecting angle of said light deflecting means therein.

13. An ophthalmologic apparatus according to claim 12, wherein said light deflecting means comprises a mirror.

14. An ophthalmologic apparatus according to claim 10, wherein said fundus portion is a blood vessel in the fundus of the eye, and said examining means examines the bloodstream state of the blood vessel in the fundus of the eye.

15. An ophthalmologic apparatus according to claim 10, wherein said naming means has an input member for naming and inputting a plurality of fundus portions, and when the fundus portion inputted by said input member is not stored in said memory means, said control means sets a fixation position at a predetermined position.

16. An ophthalmologic apparatus according to claim 15, wherein said fixation position is a position at which the optic disc of the fundus of the eye comes to the center of a field of observation.

17. An ophthalmologic apparatus according to claim 10, wherein said naming means can designate examinee information, the right or left eye information of the eye to be examined, and fundus portion information.

18. An ophthalmologic apparatus according to claim 17, wherein when the information inputted by an input member, the information of the same examinee and the same eye is stored in said memory means and the information of the same fundus portion is not stored in said memory means, said control means controls said examining means to assume a set state based on a fundus portion corresponding to the information of the same examinee's eye stored by said memory means.

* * * * *

UNITED STATES PATENT AND TRADEMARK OFFICE
CERTIFICATE OF CORRECTION

PATENT NO. : 6,193,372 B1
DATED : February 27, 2001
INVENTOR(S) : Toshiaki Okumura et al.

Page 1 of 1

It is certified that error appears in the above-identified patent and that said Letters Patent is hereby corrected as shown below:

Column 1,
Line 14, "laser Doppler," should be -- laser-Doppler, --.

Column 2,
Lines 32 and 44, "portion." should read -- the portion. --.

Column 5,
Line 61, "of" should read -- of the --.

Column 6,
Lines 25 and 31, "fixation reference" should read -- fixation-reference --.
Line 47, "to substantially" should read -- substantially to --.

Column 8,
Line 53, "of" should read -- of the --.
Line 62, "fixation reference" should read -- fixation-reference --.

Column 10,
Line 17, "fixation reference" should read -- fixation-reference --.
Line 19, "subtantially" should read -- substantially at --.

Column 11,
Lines 12 and 26, "fixation reference" should read -- fixation-reference --.

Column 12,
Line 18, "fixation reference" should read -- fixation-reference --.

Signed and Sealed this

Twenty-ninth Day of January, 2002

Attest:

*Attesting Officer*

JAMES E. ROGAN
*Director of the United States Patent and Trademark Office*